United States Patent
Takahashi

(10) Patent No.: US 10,582,859 B2
(45) Date of Patent: Mar. 10, 2020

(54) MEMS PRESSURE SENSOR AND METHOD FOR POSITIONING MEMS PRESSURE SENSOR USING TWO FILM SHEETS

(71) Applicant: ACT MEDICAL SERVICE CO., LTD., Fukushima (JP)

(72) Inventor: Shinichi Takahashi, Fukushima (JP)

(73) Assignee: ACT MEDICAL SERVICE CO., LTD., Fukushima (JP)

( * ) Notice: Subject to any disclaimer, the term of this patent is extended or adjusted under 35 U.S.C. 154(b) by 243 days.

(21) Appl. No.: 15/557,280

(22) PCT Filed: Dec. 11, 2015

(86) PCT No.: PCT/JP2015/084799
§ 371 (c)(1),
(2) Date: Sep. 11, 2017

(87) PCT Pub. No.: WO2016/147503
PCT Pub. Date: Sep. 22, 2016

(65) Prior Publication Data
US 2018/0055387 A1 Mar. 1, 2018

(30) Foreign Application Priority Data
Mar. 13, 2015 (JP) .................. 2015-050920

(51) Int. Cl.
*A61B 5/021* (2006.01)
*A61B 5/024* (2006.01)
(Continued)

(52) U.S. Cl.
CPC ............ *A61B 5/02108* (2013.01); *A61B 5/02* (2013.01); *A61B 5/022* (2013.01);
(Continued)

(58) Field of Classification Search
CPC .......... A61B 5/02; A61B 5/022; A61B 5/6833; A61B 5/684; A61B 2562/028;
(Continued)

(56) References Cited

U.S. PATENT DOCUMENTS 8,911,383 B2 12/2014 Christensen et al.
2010/0122583 A1 5/2010 Rozgo et al.
(Continued)

FOREIGN PATENT DOCUMENTS

JP 2011-505997 3/2011
JP 5017501 6/2012
(Continued)

OTHER PUBLICATIONS

Kenichi Yamagoshi et al., "Sensor for Living Body and Measurement Apparatus", edited by Japanese Society for Medical and Biological Engineering/ME Textbook Series, A-1, pp. 49 to 50, Corona Publishing Co., Ltd., published on Sep. 25, 2000 (cited in specification), English Translation only.
(Continued)

*Primary Examiner* — Christine H Matthews
*Assistant Examiner* — Joshua Daryl D Lannu
(74) *Attorney, Agent, or Firm* — Wenderoth, Lind & Ponack, L.L.P.

(57) ABSTRACT

An MEMS pressure sensing apparatus includes an MEMS pressure sensor, and first and second film sheets. The MEMS pressure sensor has a first space on a side of a pressure detection surface of a diaphragm, and has the diaphragm. The first film sheet is placed on and in contact with a part under measurement so as to support the MEMS pressure sensor, and has a second space communicating with the first space and having a size in a direction parallel to the pressure detection surface. The second film sheet has a third space with a size in a direction parallel to the pressure detection
(Continued)

surface for positioning the MEMS pressure sensing apparatus on the part under measurement, and is placed such that an area of the part under measurement is located in the third space before the MEMS pressure sensing apparatus is placed on the part under measurement.

8 Claims, 8 Drawing Sheets

(51) Int. Cl.
- *G01L 19/00* (2006.01)
- *A61B 5/022* (2006.01)
- *A61B 5/02* (2006.01)
- *A61B 5/00* (2006.01)

(52) U.S. Cl.
CPC .......... *A61B 5/02444* (2013.01); *A61B 5/684* (2013.01); *A61B 5/6833* (2013.01); *G01L 19/00* (2013.01); *A61B 5/6824* (2013.01); *A61B 5/6842* (2013.01); *A61B 2562/028* (2013.01); *A61B 2562/0247* (2013.01)

(58) Field of Classification Search
CPC .............. A61B 5/6824; A61B 5/02108; A61B 5/02444; A61B 2562/0247; A61B 5/6842; G01L 19/00

See application file for complete search history.

(56) References Cited

U.S. PATENT DOCUMENTS

| | | | |
|---|---|---|---|
| 2011/0031566 A1* | 2/2011 | Kim | ................... B81C 1/00158 257/419 |
| 2012/0289839 A1 | 11/2012 | Takenoshita et al. | |
| 2013/0079648 A1 | 3/2013 | Fukuzawa et al. | |
| 2017/0281028 A1 | 10/2017 | Sanpei et al. | |

FOREIGN PATENT DOCUMENTS

| | | |
|---|---|---|
| JP | 2013-70732 | 4/2013 |
| WO | 2012/101951 | 8/2012 |
| WO | 2015/170376 | 11/2015 |

OTHER PUBLICATIONS

International Search Report dated Feb. 2, 2016 in International (PCT) Application No. PCT/JP2015/084799.

Kenichi Yamagoshi et al., "Sensor for Living Body and Measurement Apparatus", edited by Japanese Society for Medical and Biological Engineering/ME Textbook Series, A-1, pp. 49 to 50, Corona Publishing Co., Ltd., published on Sep. 25, 2000 (cited in specification).

International Preliminary Report on Patentability dated Sep. 19, 2017 in International Application No. PCT/JP2015/084799.

Extended European Search Report dated Oct. 2, 2018 in European Application No. 15885595.7.

\* cited by examiner

MEMS PRESSURE SENSOR AND METHOD FOR POSITIONING MEMS PRESSURE SENSOR USING TWO FILM SHEETS

TECHNICAL FIELD

The present invention relates to a micro electro mechanical system (hereinafter, referred to as MEMS) pressure sensing apparatus, a pressure measuring system using the same, and a method of positioning an MEMS pressure sensor.

BACKGROUND ART

For example, Patent Document 1 discloses a measuring system, which measures a pulse pressure of, for example, a radial artery part using an optical sensor.

In particular, the invention according to Patent Document 1 is a blood vessel pulse wave measurement system, which performs blood vessel pulse wave measurement using an optical probe circuit provided with an optical probe. The blood vessel pulse wave measurement system includes a light emitting element and a light receiving element, where the light emitting element radiates light to a blood vessel through a skin, and the light receiving element receives, through the skin, reflected light from the blood vessel or transmitted light through the blood vessel. The blood vessel pulse wave measurement system further includes a drive circuit for driving the light emitting element based on an input drive signal; and a detection circuit for converting the light received by the light receiving element into an electrical signal, and outputting the same signal. The blood vessel pulse wave measurement system further includes measurement means, that directly and synchronously feeds back an electrical signal to the drive circuit as a drive signal to generate a self-oscillation signal from the detection circuit, and measures the self-oscillation signal as a blood vessel pulse wave signal. The blood vessel pulse wave measurement system further includes control means for controlling an operating point of at least one of the detection circuit and the drive circuit such that the self-oscillation signal substantially reaches a maximum level thereof.

FIG. 1 is a schematic view showing a configuration example of a pulse wave blood pressure meter system according to a conventional example, FIG. 1(a) is a vertical sectional view seen from a side of an MEMS pressure sensor 220, FIG. 1(b) is a bottom view seen from a contact surface in contact with a wrist, and FIG. 2 is a vertical sectional view showing a state of measurement when the MEMS pressure sensor 220 of FIG. 1 is brought into close contact with a radial artery part 7 of a wrist 8 (See, for example, Patent Document 2).

Referring to FIG. 1, the MEMS pressure sensor 220 is connected to a pulse wave blood pressure meter main unit 210 via connectors 211a and 211b by a cable to measure a blood pressure on a basis of a blood vessel pulse wave signal by a known method. In this case, as shown in FIG. 2, a blood pressure of a person under measurement can be measured by bringing the MEMS pressure sensor 220 into close contact with the radial artery part 7 of the wrist 8, and then sensing a pressure variation of a radial arterial pressure detected by the MEMS pressure sensor 220 as a pressure/voltage converted voltage signal so as to be converted into a blood pressure in a manner of making a voltage signal correspond to a standard blood pressure value measured in advance.

PRIOR ART DOCUMENTS

Patent Documents

[Patent Document 1] Japanese Patent No. JP5017501B1
[Patent Document 2] International Application Publication No. WO2012/101951A Non-Patent Document

[Non-Patent Document 1] Kenichi Yamagoshi and Tatsuo Togawa, "Sensor for Living Body and Measurement Apparatus", edited by Japanese Society for Medical and Biological Engineering/ME Textbook Series, A-1, pp. 49 to 50, Corona Publishing Co., Ltd., published on Sep. 25, 2000.

SUMMARY OF THE INVENTION

Problems to be Solved by the Invention

However, because a diameter of a pressure sensing cavity hole 220h of the MEMS pressure sensor 220 is very small such as an order of 1 mm, this leads to the following problems:

(1) A signal waveform from the MEMS pressure sensor 220 has a low amplitude, and includes a lot of noise, a signal quality is extremely low, and a signal-to-noise power ratio (S/N ratio) is extremely low.

(2) Since an area of the radial artery part 7 is very small, a locational range on which a sensing portion of the MEMS pressure sensor 220 is placed is extremely small.

An object of the present invention is to solve the foregoing problems and to provide an MEMS pressure sensor and a pressure measuring system using the same, and a method of positioning the MEMS pressure sensor, the MEMS pressure sensor being capable of positioning a sensing portion of the MEMS pressure sensor to, for example, an area of the radial artery part 7 more precisely as compared with the conventional example and being capable of obtaining an S/N ratio higher than that of the conventional example.

Means for Dissolving the Problems

According to a first aspect of the present invention, there is provided an MEMS pressure sensing apparatus including an MEMS pressure sensor, and a first film sheet. The MEMS pressure sensor has a first space on a side of a pressure detection surface of a diaphragm, has the diaphragm for detecting a pressure using the pressure detection surface facing the first space, and outputs an electrical signal corresponding to the detected pressure. The first film sheet is placed on and in contact with a part under measurement so as to support the MEMS pressure sensor, and has a second space communicating with the first space and having a size in a direction parallel to the pressure detection surface, where the size of the first film sheet being larger than the first space. The MEMS pressure sensing apparatus further includes a second film sheet having a third space with a size in a direction parallel to the pressure detection surface for positioning the MEMS pressure sensing apparatus on the part under measurement, and the second film sheet is placed such that an area of the part under measurement is located in the third space before the MEMS pressure sensing apparatus is placed on the part under measurement.

In the above-mentioned MEMS pressure sensing apparatus, when the MEMS pressure sensing apparatus is placed on the part under measurement via the second film sheet, then the first space, the second space and the third space are sealed to be a sealed space, so that a pressure of the part under measurement is transmitted to the diaphragm of the MEMS pressure sensor via the first space, the second space, and the third space, and then, the MEMS pressure sensor detects the pressure.

In addition, in the above-mentioned MEMS pressure sensing apparatus, the first space, the second space and the third space have bottom surfaces substantially parallel to the pressure detection surface of the diaphragm, respectively, and have substantially tubular or oval tubular shapes coaxial to each other.

Further, in the above-mentioned The MEMS pressure sensing apparatus, a diameter of the bottom surface of the third space is larger than a diameter of the bottom surface of the second space.

Still further, in the above-mentioned MEMS pressure sensing apparatus, the diameter of the bottom surface of the second space is larger than a diameter of the bottom surface of the first space.

In addition, in the above-mentioned MEMS pressure sensing apparatus, the first and second film sheets are adhesive sheets, respectively.

According to a second aspect of the present invention, there is provided a pressure measuring system including the above-mentioned MEMS pressure sensing apparatus, and a pressure measurement unit. The pressure measuring unit calculates a pressure value based on an electrical signal from the MEMS pressure sensing apparatus with reference to a relationship between an electrical signal level and a pressure value measured in advance, and outputs the calculated pressure value.

In the above-mentioned pressure measuring system, the third space of the MEMS pressure sensing apparatus is provided to be close to a blood vessel of the part under measurement so as to be able to detect a pressure, and the pressure measuring unit calculates and outputs a pulse pressure value which is the pressure value.

According to a third aspect of the present invention, there is provided a method of positioning an MEMS pressure sensing apparatus. The MEMS pressure sensing apparatus includes an MEMS pressure sensor, and a first film sheet. The MEMS pressure sensor has a first space on a side of a pressure detection surface of a diaphragm, has the diaphragm for detecting a pressure using the pressure detection surface facing the first space, and the MEMS pressure sensor outputs an electrical signal corresponding to the detected pressure. The first film sheet is placed on and in contact with a part under measurement so as to support the MEMS pressure sensor, has a second space communicating with the first space, and has a size in a direction parallel to the pressure detection surface, where the size of the first film sheet being larger than the first space. The method of positioning the MEMS pressure sensing apparatus includes the steps of:

using a second film sheet having a third space with a size in a direction parallel to the pressure detection surface to place the second film sheet on an area of the part under measurement such that the area of the part under measurement is located in the third space; and subsequently, placing the MEMS pressure sensor having the first film sheet on the second film sheet such that the second space is located in the third space, thus positioning the MEMS pressure sensing apparatus on the part under measurement.

Effects of the Invention

According to the MEMS pressure sensor and the pressure measuring system using the same, and the method of positioning the MEMS pressure sensor according to the present invention, it is possible to more precisely position the sensing portion of the MEMS pressure sensor to an area of the radial artery part 7 as compared with a conventional example and to obtain an S/N ratio higher than that of the conventional example.

BRIEF DESCRIPTION OF THE DRAWINGS

FIG. 1(a) represents a vertical sectional view seen from a side of an MEMS pressure sensor 220, and FIG. 1(b) represents a bottom view seen from a contact surface in contact with a wrist.

FIG. 8 shows an output signal waveform of the MEMS pressure sensor 220, and FIG. 8(b) FIG. 8 shows a signal waveform obtained when the output signal is passed through a low pass filter.

FIG. 9 shows an output signal waveform of the MEMS pressure sensor unit 40A, and FIG. 9(b) FIG. 9 shows a signal waveform obtained when the output signal is passed through a low pass filter.

MODE FOR CARRYING OUT THE INVENTION

Figure 1:
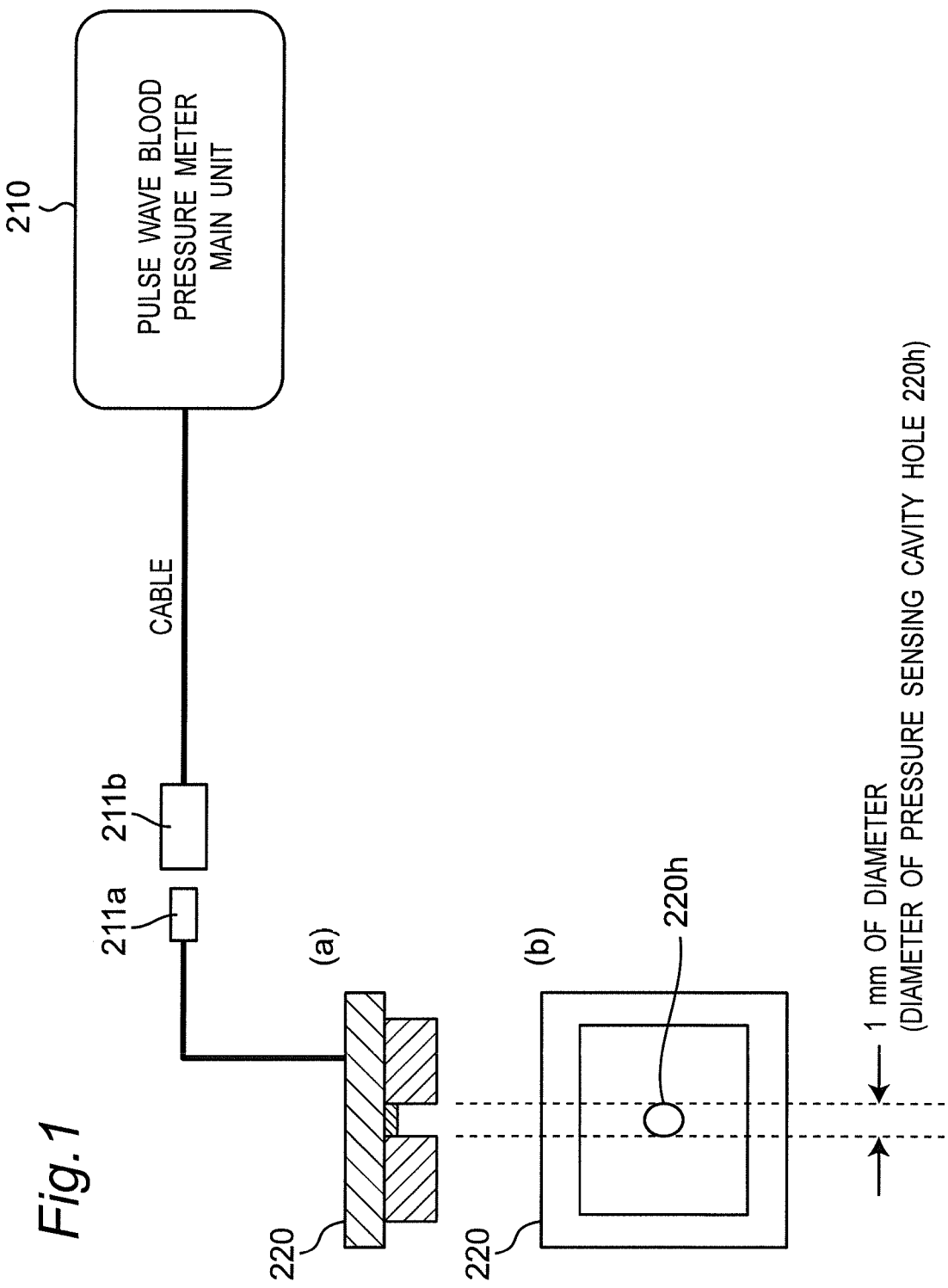
FIG. 1 is a schematic view showing a configuration example of a pulse wave blood pressure meter system according to a conventional example, where
Figure 2:
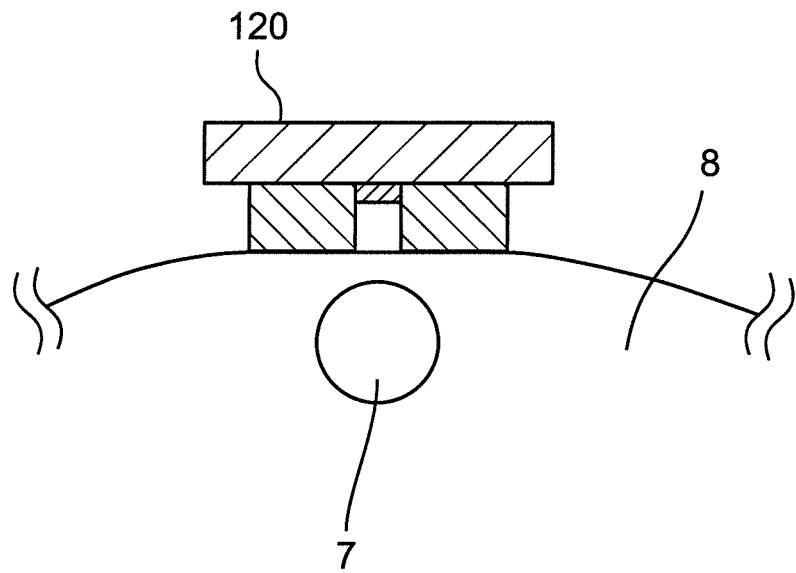
FIG. 2 is a vertical sectional view showing a state of measurement where the MEMS pressure sensor 220 of FIG. 1 is brought into close contact with a radial artery part 7 of a wrist 8.

In the following, embodiments according to the present invention will be described with reference to the drawings. In the following respective embodiments, the same components are denoted by the same reference characters.

First Embodiment

Figure 3A:
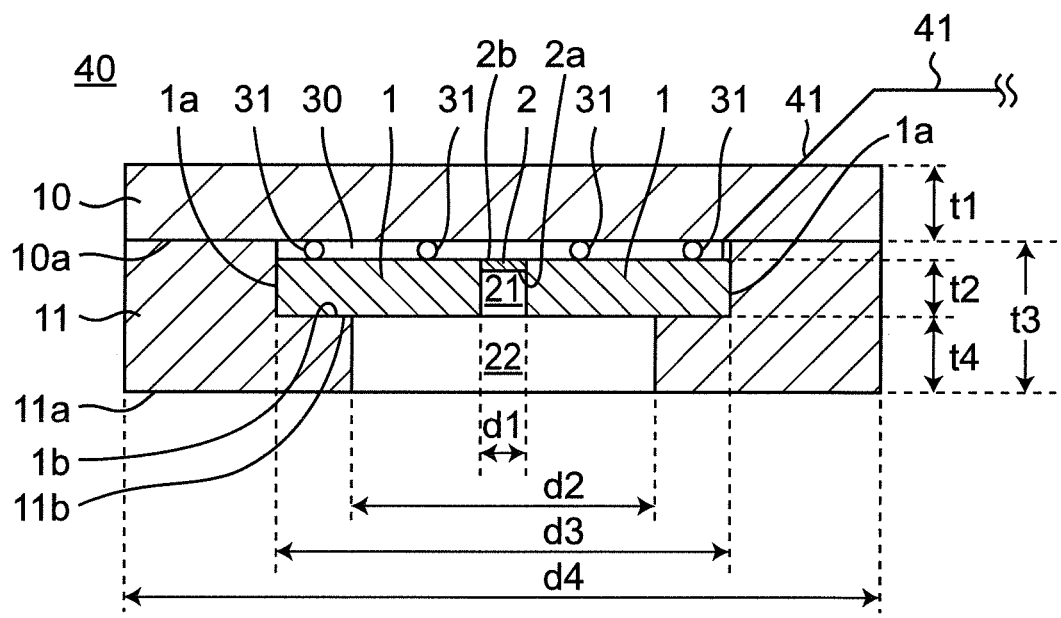
FIG. 3A is a vertical sectional view showing a configuration of a pressure sensor unit 40 according to a first embodiment of the present invention.
Figure 3B:
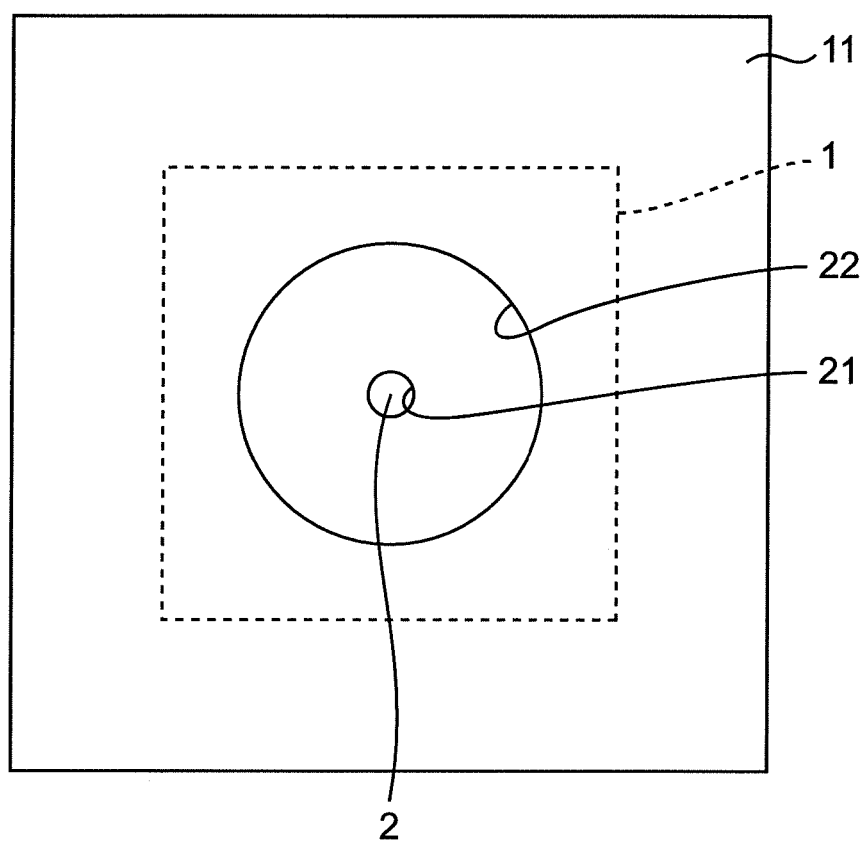
FIG. 3B is a bottom view of the pressure sensor unit 40 in FIG. 3A.

FIG. 3A is a vertical sectional view showing a configuration of a pressure sensor unit 40 according to a first embodiment of the present invention, and FIG. 3B is a bottom view of the pressure sensor unit 40 in FIG. 3A.

Referring to FIGS. 3A and 3B, an MEMS pressure sensor 1 is fixed, by a plurality of solder balls 31, to a center part of a lower side of a square plate-shaped dielectric substrate (may be a semiconductor substrate) 10 with a thickness of t1 and a width of d4 as a dielectric substance made of, for example, glass or epoxy. A space 30 is formed to be as large as a thickness of the solder balls 31. The MEMS pressure sensor 1 has a square plate-shape with, for example, a width of d3 and has a diaphragm 2 provided in a center part thereof, which is a pressure detection surface 2a having, for example, a round or oval shape. On the side of a surface 2b opposed to the pressure detection surface 2a of the diaphragm 2, the above space 30 is formed. The diaphragm 2 has a thickness smaller than a thickness t2 of the MEMS pressure sensor 1 in proximity of an upper most part of the MEMS pressure sensor 1, and has a space 21, which is, for example, a tubular or oval tubular hole formed on a lower side of the diaphragm 2. The space 21 is sealed against the diaphragm 2 and has a lower side direction opened, so that the space 21 and the space 30 fail to communicate with each other. The MEMS pressure sensor 1, which has the space 21 with the height of t2 provided on the side of the pressure detection surface 2a of the diaphragm 2, detects a pressure using the pressure detection surface 2a facing the space 21, and outputs an electrical signal corresponding to the detected pressure via a cable 41 inserted through the dielectric substrate 10.

In contact with a part 10a of a lower surface of the dielectric substrate 10 and a side surface 1a and a part of a lower surface 1b of the MEMS pressure sensor 1, a pad 11 with the thickness t3, which is, for example, a double-sided adhesive sheet, is adhered, the pad 11 supporting the MEMS pressure sensor 1 and the dielectric substrate 10. In this case, support by the pad 11 is realized by a bottom surface 11b of a space in a center part of an upper part thereof with a thickness (t3 to t4) (the center part having a hole of a downward space 22 to be described later). Then, the pad 11 has a bottom surface 11a thereof placed on and in contact with a part under measurement which is, for example, a radial artery part 7 of a wrist 8 of a person under measurement (See FIG. 5) and has the space 22, which is a through hole communicating with the space 21 in the center part of the pad 11 and having a size in a direction parallel to the pressure detection surface 2a and larger than the space 21. In this case, the space 21 and the space 22 have bottom surfaces substantially parallel to, for example, the pressure detection surface 2a of the diaphragm 2 and have, for example, substantially tubular or oval tubular shapes coaxial to each other, or polygonal shapes such as a square, rectangular shapes and the like. In the embodiment, the bottom surface of the space 22 is configured to have a diameter d2 larger than a diameter d1 of the bottom surface of the space 21.

When thus configured pressure sensor unit 40 is placed on and in contact with, for example, a part under measurement which is the radial artery part 7 of the wrist 8 of a person under measurement (See FIG. 5), the space 21 and the space 22 are sealed to be a sealed space, so that a pressure of the part under measurement is transmitted to the diaphragm 2 of the MEMS pressure sensor 1 via the space 21 and the space 22, and the MEMS pressure sensor 1 detects the pressure. A pressure detection signal of the MEMS pressure sensor 1 is outputted via the cable 41.

Figure 4:
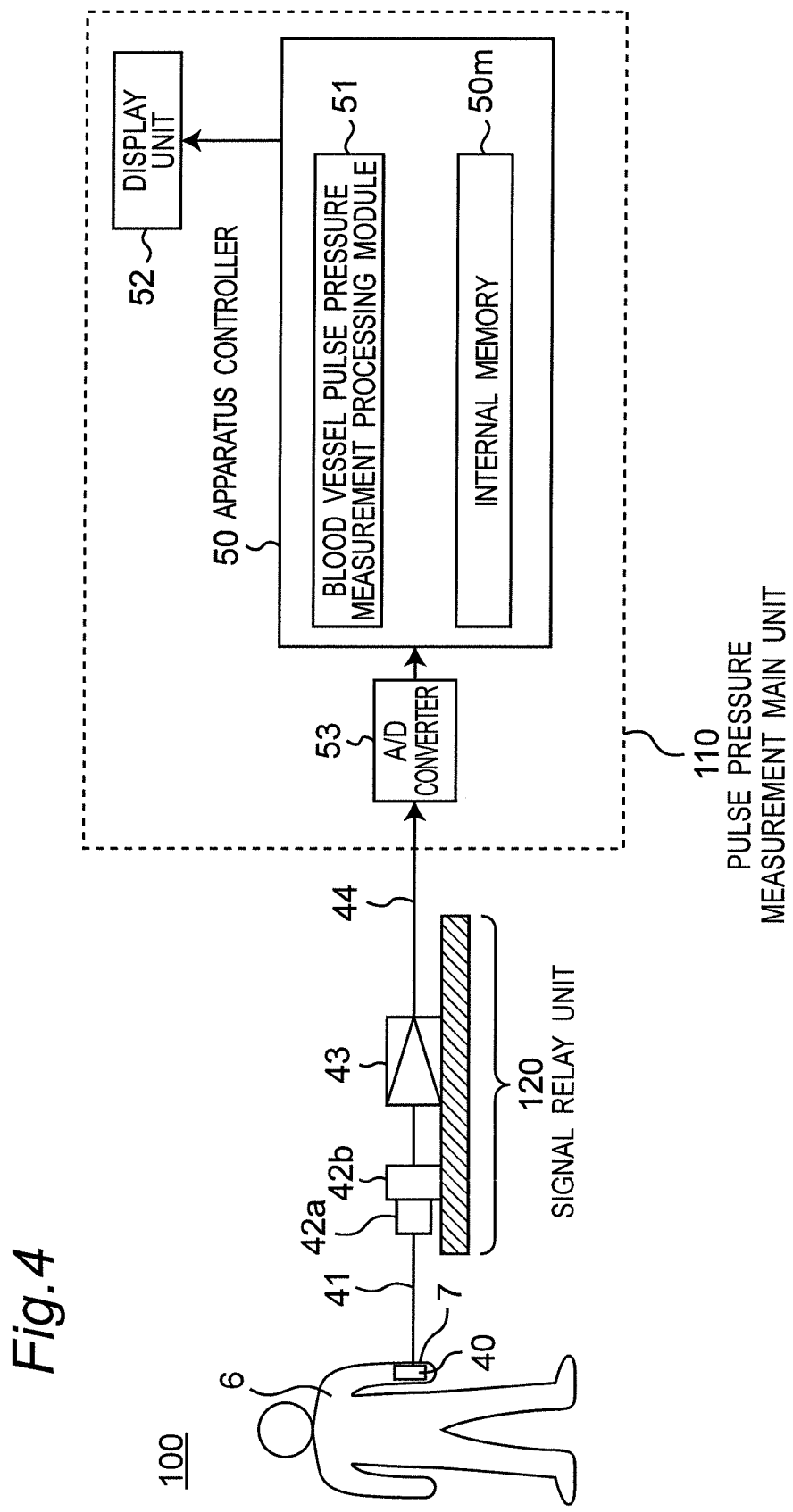
FIG. 4 is a block diagram showing a configuration of a pulse pressure measuring system 100 using the pressure sensor unit 40 in FIG. 3A.

FIG. 4 is a block diagram showing a configuration of a pulse pressure measuring system 100 using the pressure sensor unit 40 in FIG. 3A.

Referring to FIG. 4, the pressure detection signal from the pressure sensor unit 40 is input to a signal amplifier 43 of a signal relay unit 120 via the cable 41, and connectors 42a and 42b, the pressure sensor unit 40 being placed such that the space 22 of the pressure sensor unit 40 is close to, for example, the radial artery part 7 of the person under measurement 6 so as to be able to detect a pressure. The signal amplifier 43 amplifies the input pressure detection signal and inputs the amplified signal to an A/D converter 53 of a pulse pressure measurement main unit 110 via a cable 44.

The pulse pressure measurement main unit 110 is configured with an apparatus controller 50 formed of, for example, a digital computer and having a blood vessel pulse pressure measurement processing module 51 and an internal memory 50m; a display unit 52 such as, for example, a liquid crystal display; and the A/D converter 53. The A/D converter 53 outputs the input pressure detection signal to the apparatus controller 50 after A/D converting the same into digital data. By executing processing of the blood vessel pulse pressure measurement processing module 51, the apparatus controller 50 converts the digital data of the pressure detection signal into a pulse pressure value by using a signal level to a pressure value correction table (indicative of a relationship between an electrical signal level of the pressure detection signal and a pressure value) measured and stored in advance in the internal memory 50m, and outputs the obtained value to the display unit 52 to display the same. In this case, the apparatus controller 50 calculates a blood vessel pulse wave signal by executing the above blood vessel pulse pressure measurement processing in real time to display the same on the display unit 52.

Figure 5:
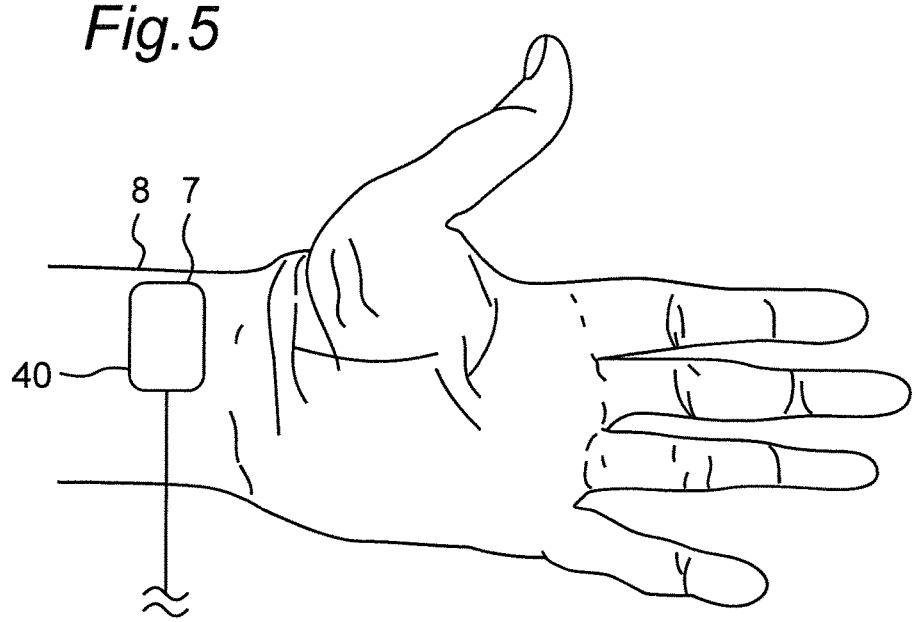
FIG. 5 is a perspective view showing the pressure sensor unit 40 in FIG. 3A when the pressure sensor unit 40 is attached to the radial artery part 7 of a person under measurement 6.

FIG. 5 is a perspective view showing the pressure sensor unit 40 in FIG. 3A when the pressure sensor unit 40 is attached to the radial artery part 7 of a person under measurement 6. As is clear from FIG. 5, the pressure sensor unit 40 is attached to the radial artery part 7 of the person under measurement 6 to measure a pulse pressure.

The inventors have made samples of the pressure sensor unit 40 and the pulse pressure measuring system 100 according to the embodiment of the present invention. A design result was obtained that the diameter d1 of the diaphragm 2 (the space 21) of the MEMS pressure sensor 1 in the pressure sensor unit 40 was most preferably on the order of 1 mm. In this case, the length d4 of one side of each of the dielectric substrate 10 and the pad 11 was set to be 3 to 4 mm and the diameter d2 of the space 22 was set to be 2 to 3 mm. The thickness t2 of the MEMS pressure sensor 1 was 400 μm and a thickness of a lower portion of the pad 11 was 0.5 to 1 mm. Specifically, when there is no space 22 similarly to the conventional art, a blood vessel needs to be positioned within a range of 1 mm, which is the diameter d1 of the diaphragm 2 of the MEMS pressure sensor 1, and when the position deviates, no pulse pressure can be detected. However, in the present embodiment, provision of the space 22 enables a pulse pressure to be reliably detected even when the diaphragm 2 of the MEMS pressure sensor 1 deviates on the order of 1 to 1.5 mm as long as the deviation is within a range of the space 22. Additionally, since the MEMS pressure sensing apparatus of the present embodiment enables detection of a pulse pressure without applying a pressure, bloodless blood pressure pulse wave measurement can be conducted for a long period of time. Additionally, it is possible, in a manner similar to that of the conventional example, to measure a blood pressure of a person under measurement using the measurement method of Patent Document 2.

When thus configured pressure sensor unit 40 according to the present embodiment is placed on the part under measurement, the space 21 and the space 22 are sealed to be a sealed space, so that a pressure of the part under measurement is transmitted to the diaphragm 2 of the MEMS pressure sensor 1 via the space 21 and the space 22, and the MEMS pressure sensor 1 detects the pressure. Accordingly, even when the position of the MEMS pressure sensor 1 deviates from a measurement position, it is possible to precisely measure a pressure of the part under measurement. Additionally, since it is not necessary to apply a pressure to the part under measurement, it is possible to measure, for example, a bloodless blood pressure pulse wave for a long period of time.

Second Embodiment

Figure 6:
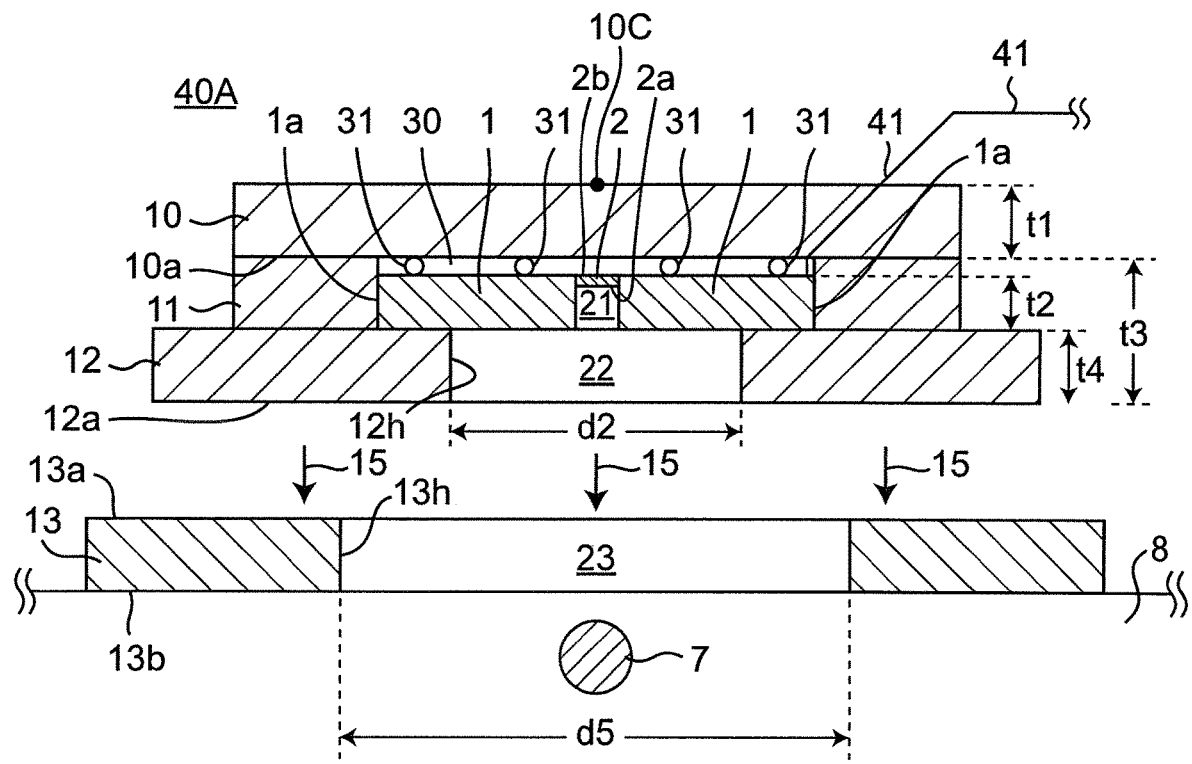
FIG. 6 is a vertical sectional view showing a configuration of a pressure sensor unit 40A according a second embodiment of the present invention.

FIG. 6 is a vertical sectional view showing a configuration of a pressure sensor unit 40A according a second embodiment of the present invention. Referring to FIG. 6, the pressure sensor unit 40A according to the second embodiment is different from the pressure sensor unit 40 in FIG. 3A in the following points.

(1) A bottom surface portion of a pad 11 is removed, to which a film sheet 12 with a thickness t4 is bonded. In this case, in a center part, the film sheet 12 has a space 22 formed by a pressure sensing cavity hole 12h.

(2) For positioning the pressure sensor unit 40A having the film sheet 12, a film sheet 13 is further provided which is to be bonded to a radial artery part 7 of a wrist 8 in advance. In a center part, the film sheet 13 has a space 23 formed by a pressure sensing cavity hole 13h, the space having a size in a direction parallel to a pressure detection surface. In this case, for facilitating adhesion of the film sheet 13 to the radial artery part 7, a diameter d5 of the pressure sensing cavity hole 13h is larger than a diameter d2 of the pressure sensing cavity hole 12h of the film sheet 12. In the configuration example, d5 is 5 mm and d2 is 3 mm. Additionally, spaces 21, 22, and 23 configure the sealed space described in the first embodiment.

(3) In a center part of an upper surface of a dielectric substrate 10 in the pressure sensor unit 40A, a mark 10C indicative of the center is preferably painted.

Subsequently, description will be made in the following of the pressure sensor unit 40A and a procedure of a method of positioning the pressure sensor unit 40A using the film sheet 13.

Figure 8:
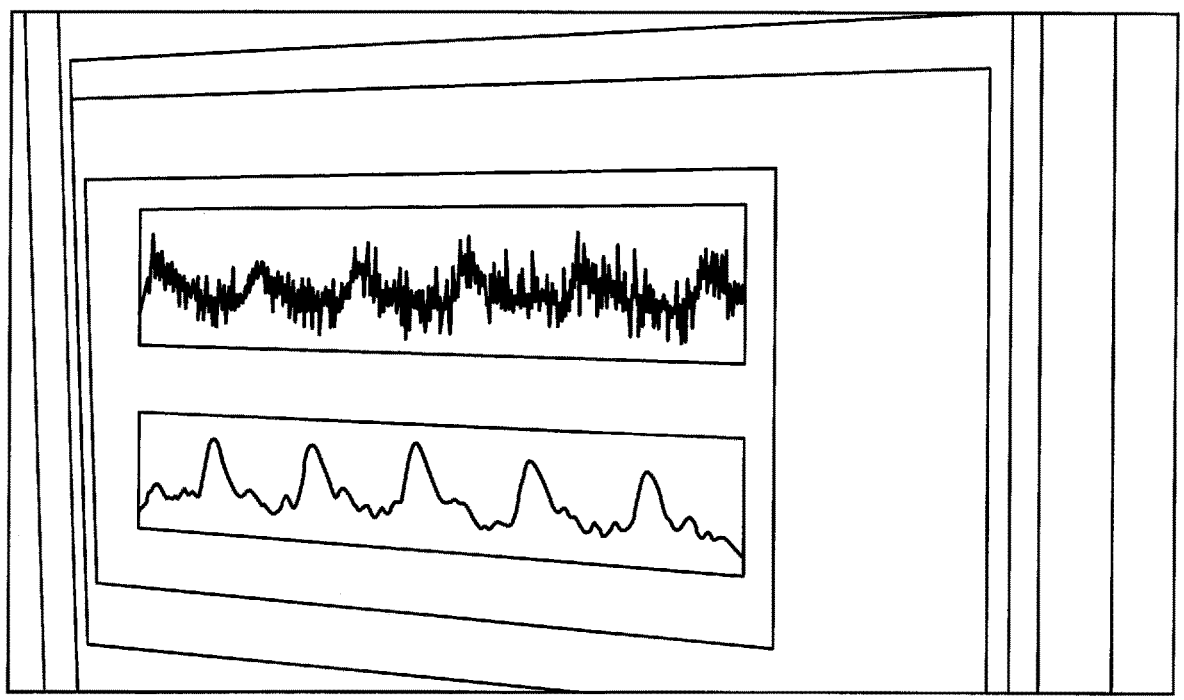
FIG. 8 is a photograph of signal waveforms of an experimental result obtained when a pulse wave signal of a radial artery part is measured using the MEMS pressure sensor 220 according to the conventional example in FIG. 1, where FIG. 8(a)

In the pulse wave measuring system using the pressure sensor unit 40A of the MEMS pressure sensor, for sensing a blood vessel pulsation at a higher S/N ratio, it is necessary to precisely dispose the pressure sensor unit 40A on the radial artery part 7 of the wrist 8 of a person under measurement. For efficiently executing this operation, the following procedure as shown in FIG. 8 is used.

(Step A) First of all, the film sheet 13 is adhered to a position of the radial artery part 7 (preferably, a part first confirmed and marked as a position at which pulse can be taken). In this case, the film sheet 13 is positioned and adhered such that a bonding lower surface 13b of the film sheet 13 is bonded to a surface of skin of the radial artery part 7, and a center part of the pressure sensing cavity hole 13h of the film sheet 13 is located at the radial artery part 7.

(Step B) Subsequently, to an upper surface 13a of the film sheet 13, the film sheet 12 of the pressure sensor unit 40A is adhered. In this case, the pressure sensor unit 40A having the film sheet 12 is positioned such that the mark 10C is located at the center part of the pressure sensing cavity hole 13h, i.e., such that a center part of the pressure sensing cavity hole 12h of the film sheet 12 is located at the center part of the pressure sensing cavity hole 13h.

Figure 7:
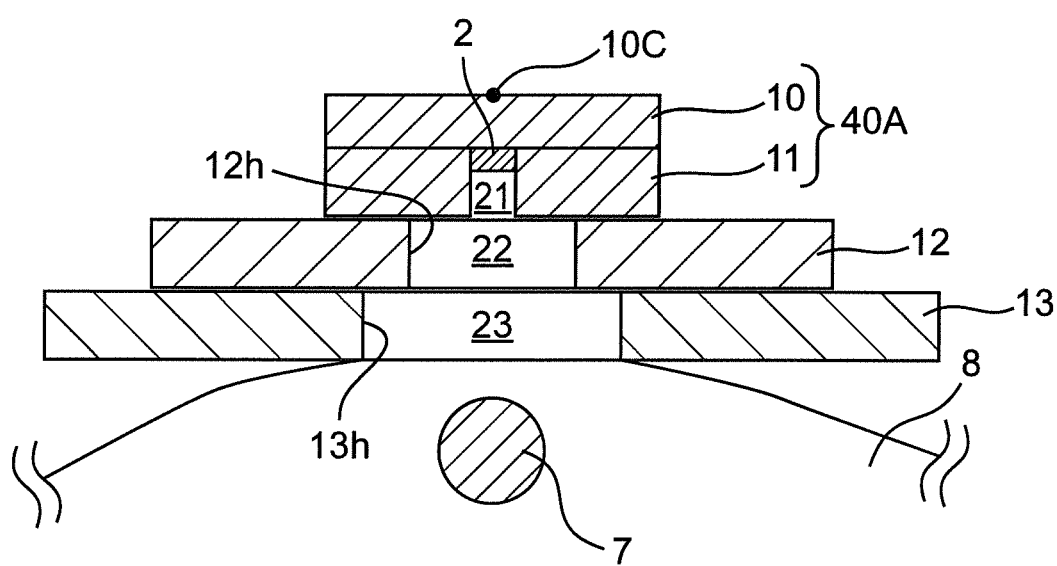
FIG. 7 is a vertical sectional view showing the pressure sensor unit 40A in FIG. 6 when the pressure sensor unit 40A is attached to a radial artery part 7 of a person under measurement 6.

FIG. 7 is a vertical sectional view showing the pressure sensor unit 40A in FIG. 6 when the pressure sensor unit 40A is attached to the radial artery part 7 of a person under measurement 6. Specifically, FIG. 7 shows a state after the above Step B.

As described in the foregoing, a two-stage adhering step enables the sealed spaces 21, 22, and 23 to be reliably formed for sensing pulsation by the MEMS sensor. In a manner similar to the pressure sensor unit 40 according to the first embodiment, in the pressure sensor unit 40A of the second embodiment, when the pressure sensor unit 40A is placed on a part under measurement, the spaces 21, 22, and 23 are sealed to be a sealed space, so that a pressure of the part under measurement is transmitted to a diaphragm 2 of an MEMS pressure sensor 1 via the spaces 21, 22, and 23, and the MEMS pressure sensor 1 detects the pressure. Accordingly, even when the position of the MEMS pressure sensor 1 deviates from a measurement position, it is possible to precisely measure the pressure of the part under measurement. Additionally, since it is not necessary to apply a pressure to the part under measurement, it is possible to measure, for example, a bloodless blood pressure pulse wave for a long period of time.

EXAMPLES

FIG. 8 is a photograph of signal waveforms of an experimental result obtained when a pulse wave signal of a radial artery part is measured using the MEMS pressure sensor 220 according to the conventional example in FIG. 1, where FIG. 8 shows an output signal waveform of the MEMS pressure sensor 220, and FIG. 8 shows a signal waveform obtained when the output signal is passed through a low pass filter. Additionally, FIG. 9 is a photograph of signal waveforms of an experimental result obtained when a pulse wave signal of a radial artery part is measured using the MEMS pressure sensor unit 40A according to the second embodiment in FIG. 6, where FIG. 9 shows an output signal waveform of the MEMS pressure sensor unit 40A, and FIG. 9 shows a signal waveform obtained when the output signal is passed through a low pass filter.

Figure 9:
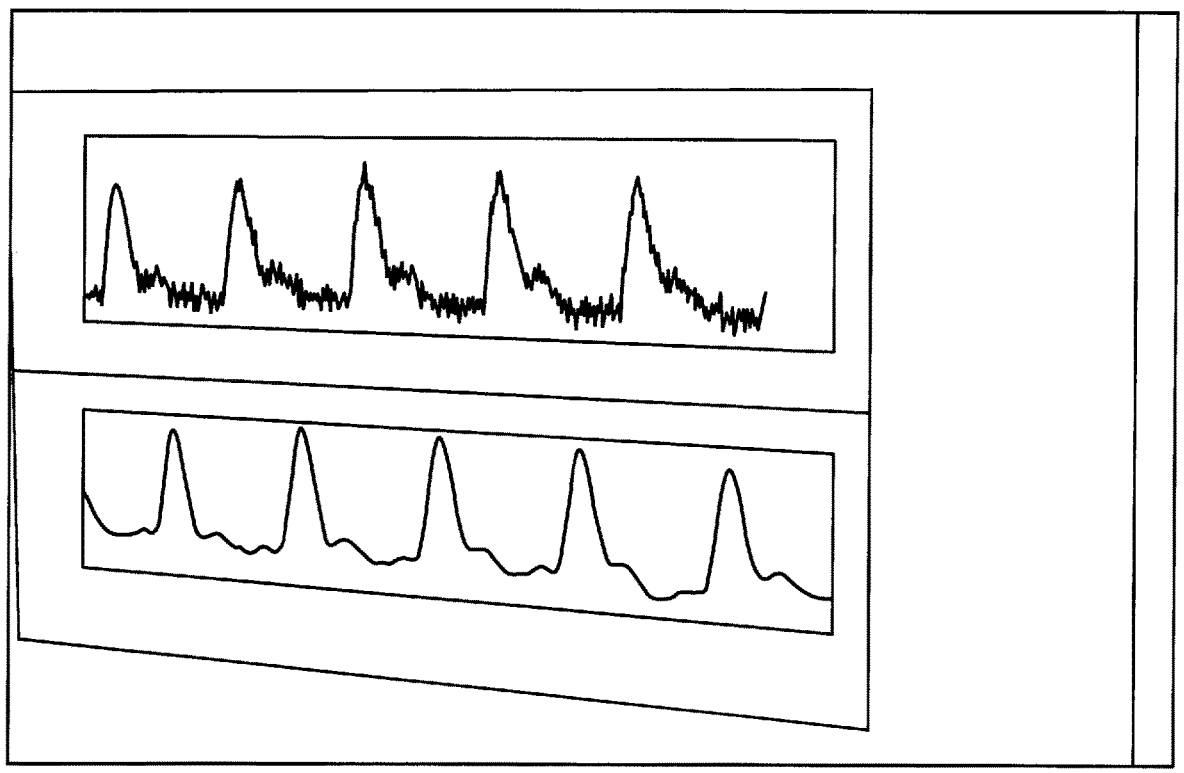
FIG. 9 is a photograph of signal waveforms of an experimental result obtained when a pulse wave signal of a radial artery part is measured using the MEMS pressure sensor unit 40A according to the second embodiment in FIG. 6, where FIG. 9(a)

As is clear from comparison between FIGS. 8 and 9, regarding the signal waveform of the second embodiment, both an output waveform of the sensor and a signal waveform obtained after passing through a low pass filter can be measured with an S/N ratio drastically increased as compared with a signal waveform of a conventional example.

Although the foregoing present embodiments have been described with respect to a pulse pressure measuring system and a blood pressure measuring system, the present invention is not limited thereto and is applicable to a pressure measuring system and a blood pressure measuring system, that measure a pulse pressure of other animal than a human being and a common pressure. Additionally, the pressure sensor units 40 and 40A can be used as a pressure sensing apparatus to detect not only a pulse pressure of a blood vessel but also a pulse pressure of other animal than a human being and detect a common pressure.

Additionally, the shapes of the spaces 21, 22, and 23 formed by the respective cavity holes may be not only tubular but also oval tubular.

INDUSTRIAL APPLICABILITY

As has been described in detail in the foregoing, according to the present invention, when the MEMS pressure sensing apparatus is placed on a part under measurement to have a sealed space, a pressure of the part under measurement is transmitted to the diaphragm of the MEMS pressure sensor via two or three spaces, so that the MEMS pressure sensor detects a pressure. Accordingly, even when a position of the MEMS pressure sensor deviates from a measurement position, it is possible to precisely measure a pressure of the part under measurement. Additionally, since it is unnecessary to apply a pressure to the part under measurement, a bloodless blood pressure pulse wave can be measured for a long period of time.

Additionally, the present invention enables the sensing portion of the MEMS pressure sensor to be positioned at an area of a radial artery part more precisely as compared with a conventional example, and an S/N ratio can be obtained which is higher than that of the conventional example.

DESCRIPTION OF NUMERICAL REFERENCES

1: MEMS pressure sensor
2: diaphragm
6: person under measurement
7: radial artery part
8: wrist
10: dielectric substrate
11: pad
12, 12A, 13: film sheet
21, 22, 23: space
31: solder ball
40, 40A: pressure sensor unit
41, 44: cable
42*a*, 42*b*: connector
43: signal amplifier
50: apparatus controller
50*m*: internal memory
51: blood vessel pulse pressure measurement processing module
52: display unit
53: A/D converter
100: pulse pressure measuring system
110: pulse pressure measurement main unit
120: signal relay unit
210: pulse wave blood pressure meter main unit
211*a*, 211*b*: connector
220: MEMS pressure sensor
220*h*: pressure sensing cavity hole

The invention claimed is:

1. A MEMS pressure sensing apparatus comprising:
a MEMS pressure sensor having a first space on a side of a pressure detection surface of a diaphragm, the MEMS pressure sensor having the diaphragm for detecting a pressure using the pressure detection surface facing the first space, the MEMS pressure sensor outputting an electrical signal corresponding to the detected pressure; and
a first film sheet placed on and in contact with a part under measurement so as to support the MEMS pressure sensor, the first film sheet having a second space communicating with the first space and having a size in a direction parallel to the pressure detection surface, a size of the first film sheet being larger than the first space,
wherein the MEMS pressure sensing apparatus further comprises a second film sheet having a third space with a size in a direction parallel to the pressure detection surface for positioning the MEMS pressure sensing apparatus on the part under measurement, the second film sheet being placed such that an area of the part under measurement is located in the third space before the MEMS pressure sensing apparatus is placed on the part under measurement,
wherein the first and second film sheets are adhesive sheets, respectively.

2. The MEMS pressure sensing apparatus as claimed in claim 1,
wherein, when the MEMS pressure sensing apparatus is placed on the part under measurement via the second film sheet, then the first space, the second space and the third space are sealed to be a sealed space, so that a pressure of the part under measurement is transmitted to the diaphragm of the MEMS pressure sensor via the first space, the second space, and the third space, and then, the MEMS pressure sensor detects the pressure.

3. The MEMS pressure sensing apparatus as claimed in claim 1,
wherein the first space, the second space and the third space have bottom portions substantially parallel to the pressure detection surface of the diaphragm, respectively, and have substantially tubular or oval tubular shapes coaxial to each other.

4. The MEMS pressure sensing apparatus as claimed in claim 1,
wherein a diameter of a bottom portion of the third space is larger than a diameter of a bottom portion of the second space.

5. The MEMS pressure sensing apparatus as claimed in claim 1,
wherein the diameter of a bottom portion of the second space is larger than a diameter of a bottom portion of the first space.

6. A pressure measuring system comprising:
a MEMS pressure sensing apparatus; and
a pressure measuring unit that calculates a pressure value based on an electrical signal from the MEMS pressure sensing apparatus with reference to a relationship between an electrical signal level and a pressure value measured in advance, and outputs the calculated pressure value,
wherein the MEMS pressure sensing apparatus comprises:
a MEMS pressure sensor having a first space on a side of a pressure detection surface of a diaphragm, the MEMS pressure sensor having the diaphragm for detecting a pressure using the pressure detection surface facing the first space, the MEMS pressure sensor outputting an electrical signal corresponding to the detected pressure; and
a first film sheet placed on and in contact with a part under measurement so as to support the MEMS pressure sensor, the first film sheet having a second space communicating with the first space and having a size in a direction parallel to the pressure detection surface, a size of the first film sheet being larger than the first space,
wherein the MEMS pressure sensing apparatus further comprises a second film sheet having a third space with a size in a direction parallel to the pressure detection surface for positioning the MEMS pressure sensing apparatus on the part under measurement, the second film sheet being placed such that an area of the part under measurement is located in the third space before the MEMS pressure sensing apparatus is placed on the part under measurement.

7. The pressure measuring system as claimed in claim 6, wherein the third space of the MEMS pressure sensing apparatus is provided to be close to a blood vessel of the part under measurement so as to be able to detect a pressure, and wherein the pressure measuring unit calculates and outputs a pulse pressure value which is the pressure value.

8. A method of positioning a MEMS pressure sensing apparatus, the MEMS pressure sensing apparatus including:

a MEMS pressure sensor having a first space on a side of a pressure detection surface of a diaphragm, the MEMS pressure sensor having the diaphragm for detecting a pressure using the pressure detection surface facing the first space, the MEMS pressure sensor outputting an electrical signal corresponding to the detected pressure; and a first film sheet placed on and in contact with a part under measurement so as to support the MEMS pressure sensor, the first film sheet having a second space communicating with the first space, the first film sheet having a size in a direction parallel to the pressure detection surface, the size of the first film sheet being larger than the first space, wherein the method of positioning the MEMS pressure sensing apparatus includes the steps of:

using a second film sheet having a third space with a size in a direction parallel to the pressure detection surface to place the second film sheet on an area of the part under measurement such that the area of the part under measurement is located in the third space; and subsequently, placing the MEMS pressure sensor having the first film sheet on the second film sheet such that the second space is located in the third space, thus positioning the MEMS pressure sensing apparatus on the part under measurement.

* * * * *